(12) United States Patent
Ota (10) Patent No.: US 7,446,796 B2
(45) Date of Patent: Nov. 4, 2008

(54) ELECTRONIC ENDOSCOPE SYSTEM

(75) Inventor: Noriko Ota, Saitama (JP)

(73) Assignee: Hoya Corporation, Tokyo (JP)

( * ) Notice: Subject to any disclaimer, the term of this patent is extended or adjusted under 35 U.S.C. 154(b) by 900 days.

(21) Appl. No.: 10/777,086

(22) Filed: Feb. 13, 2004

(65) Prior Publication Data

US 2004/0165846 A1   Aug. 26, 2004

(30) Foreign Application Priority Data

Feb. 17, 2003   (JP)   ............................. 2003-038347

(51) Int. Cl.
*A61B 1/06* (2006.01)
*A62B 1/04* (2006.01)

(52) U.S. Cl. ........................................ 348/65; 600/180

(58) Field of Classification Search ................ 348/65, 348/68, 69, 74, 72, 76; 600/110, 118, 178, 600/126, 180

See application file for complete search history.

(56) References Cited

U.S. PATENT DOCUMENTS 4,919,114 A * 4/1990 Miyazaki .................... 600/110
4,989,586 A * 2/1991 Furukawa .................... 600/110
5,622,528 A * 4/1997 Hamano et al. ............. 600/118
6,602,186 B1 8/2003 Sugimoto et al.
2002/0026099 A1* 2/2002 Adachi et al. ............... 600/178

FOREIGN PATENT DOCUMENTS

| JP | 10-108826 | 4/1998 |
|---|---|---|
| JP | 2866658 | 12/1998 |
| JP | 11-305148 | 11/1999 |
| JP | 2000-210245 | 8/2000 |
| JP | 2002-72106 | 3/2002 |

* cited by examiner

*Primary Examiner*—Gims S Philippe
(74) *Attorney, Agent, or Firm*—Greenblum & Bernstein, P.L.C.

(57) ABSTRACT

An electronic endoscope system includes an image pickup device provided at a distal end of an insertion portion; an image signal processing device; a main light source; an auxiliary light source which emits less amount of light than the light emitted from the main light source; and a light guide member which guides illumination light emitted from one of the main light source and the auxiliary light source to the distal end of the insertion portion to thereby emit the illumination light from the distal end. When the auxiliary light source emits the illumination light instead of the main light source, the image signal processing device sets the gain of the signal output from the image pickup device to a value higher than the gain of the signal when the main light source emits the illumination light, in order to process the image signal.

6 Claims, 5 Drawing Sheets

ELECTRONIC ENDOSCOPE SYSTEM

BACKGROUND OF THE INVENTION

1. Field of the Invention

The present invention relates to an electronic endoscope system having a main light source and an auxiliary light source.

2. Description of the Related Art

A high intensity lamp, such as a halogen lamp, a mercury vapor lamp or a metal halide lamp is used as a main light source of a light source apparatus for an electronic endoscope. If the light source goes off due to expiration of the service life thereof or trouble during examination or an operation using an endoscope, it is necessary to replace the light source or the light source apparatus with a new one. It is not desirable for the endoscope to stay in a body cavity of a patient during replacement of the light source.

To solve this problem, it has been proposed to provide a separate auxiliary light source in addition to a main light source made of a high intensity lamp, wherein if the main light source goes off, the auxiliary light source is used to illuminate a body cavity of a patient, so that an insertion portion of an endoscope can be entirely removed from the body cavity under the illumination by the auxiliary light source (see Japanese Patent Applications Laid-open Nos. 2000-210245, H10-108826, 2002-72106).

As the auxiliary light source is provided for emergency use and is seldom used, it is preferable that the auxiliary light source be as small as possible and tend not to deteriorate due to aging. To this end, for example, a high intensity LED can be used.

However, if the auxiliary light source is a high intensity LED, the amount of light emitted therefrom is smaller than that of the main light source, and hence, there is a possibility, during use of an electronic endoscope, that a picked-up image is too dark due to insufficient amount of light emitted from the auxiliary light source.

SUMMARY OF THE INVENTION

The present invention eliminates the drawbacks of the prior art mentioned above by providing an electronic endoscope system in which a bright and clear image can be obtained even if an auxiliary light source is used.

According to an aspect of the present invention, an electronic endoscope system is provided, including an electronic endoscope having an insertion portion; an image pickup device provided at a distal end of the insertion portion; an image signal processing device for converting a signal picked-up by and output from the image pickup device into an image signal; a main light source; an auxiliary light source which emits less amount of light than the light emitted from the main light source, instead of the main light source; and a light guide member which guides illumination light emitted from one of the main light source and the auxiliary light source to the distal end of the insertion portion to thereby emit the illumination light from the distal end. When the auxiliary light source emits the illumination light instead of the main light source, the image signal processing device sets the gain of the signal output from the image pickup device to a value higher than the gain of the signal when the main light source emits the illumination light, in order to process the image signal.

The electronic endoscope system can include a processor unit to which the electronic endoscope is detachably attached, the processor unit being provided with the image signal processing device, the main light source and the auxiliary light source. The light guide member includes a first light guide member provided in the electronic endoscope and a second light guide member provided in the processor unit, wherein the first and second light guide members are optically connected to each other when the electronic endoscope is attached to the processor unit.

According to an aspect of the present invention, an electronic endoscope system is provided, including an electronic endoscope having an insertion portion; an image pickup device provided at a distal end of the insertion portion; an image signal processing device for converting a signal picked-up by and output from the image pickup device into an image signal which can be displayed by a display device; a main light source; an auxiliary light source which emits less amount of light than the light emitted from the main light source, instead of the main light source; and a light guide member which guides illumination light emitted from one of the main light source and the auxiliary light source to the distal end of the insertion portion to thereby emit the illumination light from the distal end. The image signal processing device performs a high-speed shutter operation in which the image pickup operation and the image signal output operation are repeated at a predetermined cycle when the main light source emits the illumination light; and performs a low-speed shutter operation in which the image pickup operation and the image signal output operation are repeated at a cycle longer than the predetermined cycle when the auxiliary light source emits the illumination light instead of the main light source.

When the image signal processing device performs the low-speed shutter operation, it is desirable for the image pickup operation and the image signal output operation to be repeated at a cycle which is represented the predetermined cycle multiplied by an integer value.

It is desirable for the image signal processing device to include a memory for storing the picked-up image signals for at least one field, so that when the image signal processing device performs the low-speed shutter operation, the stored image signals for at least one field are read at the predetermined cycle and are converted into image signals which can be displayed by the display device. In another embodiment, an electronic endoscope system is provided, including an electronic endoscope having an insertion portion; an image pickup device provided at a distal end of the insertion portion; an image signal processing device for converting a signal picked-up by and output from the image pickup device into an image signal; a main light source; an auxiliary light source which emits less amount of light than the light emitted from the main light source, instead of the main light source; and a light guide member which guides illumination light emitted from one of the main light source and the auxiliary light source to the distal end of the insertion portion to thereby emit the illumination light from the distal end. When the main light source emits the illumination light, the image pickup device operates at a high-speed shutter operation mode in which the image pickup operation and the image signal output operation are repeated at a predetermined cycle, so that the image signal processing device processes the image signal output from the image pickup device after the image signal is amplified at a first gain; and when the auxiliary light source emits the illumination light instead of the main light source, the image pickup device operates at a low-speed shutter operation mode in which the image pickup operation and the image signal output operation are repeated at a cycle longer than the predetermined cycle, so that the image processing device processes the image signal output from the image pickup device after the image signal is amplified at a second gain higher than the first gain.

The present disclosure relates to subject matter contained in Japanese Patent Application No. 2003-38347 (filed on Feb. 17, 2003) which is expressly incorporated herein by reference in its entirety.

DESCRIPTION OF THE PREFERRED EMBODIMENT

Figure 1:
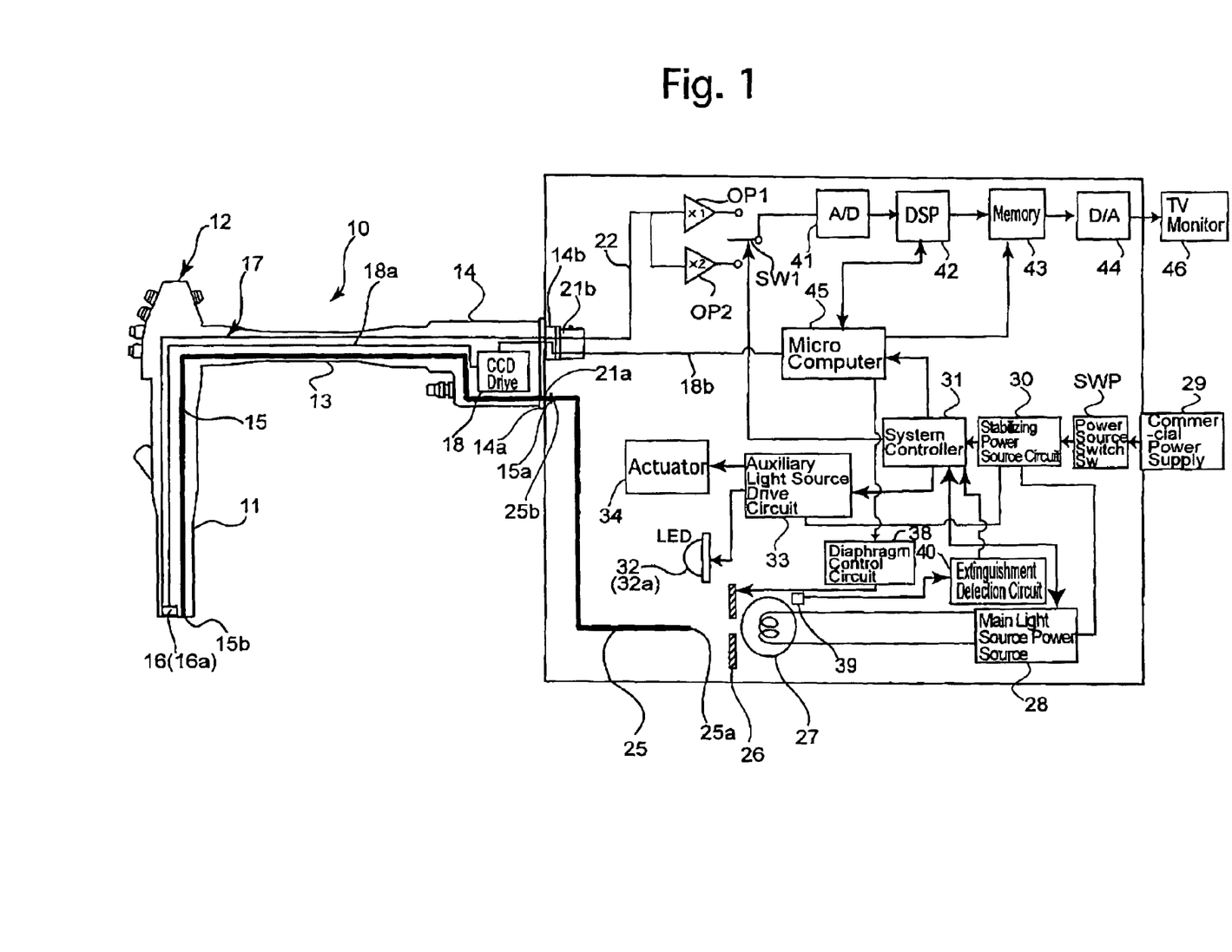
FIG. 1 is a block diagram of main components of an electronic endoscope system according to a first embodiment of the present invention.

The present invention will be discussed below with reference to the accompanying drawings. FIG. 1 shows the main components of a first embodiment of a light source apparatus applied to an electronic endoscope system, according to the present invention.

The electronic endoscope 10 is constructed from a flexible insertion portion 11, an operating portion 12 provided at a proximal end of the insertion portion 11, a universal tube 13 connected at one end thereof to the operating portion 12, and a connector portion 14 provided at the other end of the universal tube 13 and having an optical connector 14a and an electric connector 14b. The insertion portion 11 is provided on distal end thereof with a built-in electronic camera (video camera) 16 including an image pickup lens and an image pickup device (CCD) 16a, etc. The electronic camera 16 can pickup an image of an external object through a view window (object window) formed at the distal end face of the insertion portion 11. A light guide (d bundle of optical fibers/illumination light guiding device/light guide member) 15 is provided inside electronic endoscope 10 from the distal end of the insertion portion 11, i.e., inside the insertion portion 11, the operating portion 12 and the universal tube 13, and is connected at the proximal end thereof to the optical connector 14a of the connector portion 14 The insertion portion 11 is provided on the distal end face thereof with an emission end face 15b of the light guide 15, and an outlet port of forceps channel (not shown), etc. The operating portion 12 is provided with operation buttons for controlling a motion image or still image capturing operation, and a bending motion operating knob which operates a bending mechanism provided in the vicinity of the distal end of the insertion portion 11. The electronic endoscope 10 is also provided with a CCD drive circuit 18 in the connector portion 14 to drive the image pickup device 16a of the electronic camera 16 in order to carry out an image pickup operation.

A processor unit 20 includes an image signal processing system for processing an analogue signal picked up by the electronic camera 16, which includes first and second amplifiers OP1 and OP2 for amplifying the input signals at first and second gains, an A/D converter 41 which converts the amplified analogue signal output from the first amplifier OP1 or the second amplifier OP2, a DSP 42 which processes the digital signal output from the A/D converter 41, a memory 43 which stores the digital signals processed by the DSP 42 for at least one field or one frame, and a D/A converter 44 which converts the digital image signals read from the memory 43 into analogue video signals. Furthermore, the processor unit 20 includes a signal selecting switch SW1 for selecting the first and second amplifiers OP1 and OP2 in order to select a signal to be supplied to the A/D converter 41 from the first and second amplifiers OP1 and OP2. The first and second amplifiers OP1 and OP2, the A/D converter 41, the DSP 42, the memory 43, and the D/A converter 44 constitute an image signal processing device.

The processor unit 20 is also provided with a micro computer 45 which controls the components of the electronic camera 16 and the image signal processing device. Note that the micro computer 45 operates under the control of a system controller 31 which generally controls the electronic endoscope system.

A signal cable 17 is inserted in the insertion portion 11, the operating portion 12 and the universal tube 13 and is connected at one end thereof to the electronic camera 16 and at the other end thereof to a pin of an electric connector 14b of the connector portion 14. An image cable 22 is connected at one end thereof to a pin of an electric connector 21b of the connector portion 21 and at the other end thereof to each input port of the first and second amplifiers OP1 and OP2. The electronic camera 16 is connected to the input ports of the amplifiers OP1 and OP2 via the signal cable 17, the electric connector 14b of the connector portion 14, the electric connector 21b of the connector portion 21, and the image cable 22.

A TV monitor (display device) 46 which displays a visible image picked up by the electronic camera 16 via a video encoder (not shown) is connected to the D/A converter 44, so that an operator can operate the electronic camera 16 while viewing the image through the TV monitor. Note that in addition to the TV monitor, an external memory device such as a video deck for recording the image, and an image signal input terminal of a personal computer, etc., can be connected to the D/A converter 44.

As mentioned above, the light guide 15 extends from the distal end of the insertion portion 11 and is connected at the proximal end thereof (via the operating portion 12 and the universal tube 13) to the optical connector 14a of the connector portion 14. The optical connector 14a is connected to the optical connector 21a of the connector portion 21 when the connector portion 14 is connected to the connector portion 21, so that the incident end face 15a of the light guide 15 is optically connected to an emission end face 25b of a light guide 25. The other end face of the light guide 25, i.e., an incident end face 25a, is arranged so as to receive the illumination light emitted from a main light source 27. A diaphragm 26 is provided in a main light path between the main light source 27 and the incident end face 25a, so that the amount of light to be received by the incident end face 25a can be controlled by opening and closing the diaphragm 26. The diaphragm 26 is controlled by the system controller 31 via a diaphragm drive circuit 38.

The illumination light emitted from the main light source 27 and made incident upon the incident end face 25a is transmitted through the light guide 25, the emission end face 25b, the incident end face 15a, and the light guide 15, and is emitted externally from the illumination window at the distal end of the insertion portion 11 through the emission end face 15b of the light guide 15 to illuminate a body cavity.

The emission of the main light source 27 is controlled by the main light source power source 28. The main light source power source 28 controls the activation of the main light source 27 by an electric current stabilized in a stabilizing power source circuit 30 which receives the electric power supplied from a commercial power supply 29.

A high intensity lamp, such as a halogen lamp, a mercury vapor lamp, or a metal halide lamp is usually use as the main light source 27, and is mounted to a lamp socket having a reflector shade. The light emitted from the main light source 27 is effectively converged onto the incident end face 25a of the light guide 25 by a condenser lens (not shown). The main light source 27 and the light guide 25 are arranged so that the convergence point of the light from the main light source 27 is the same as the incident end face 25a.

The processor unit 20 includes an auxiliary light source 32 which irradiates illumination light in place of the main light source 27 if the main light source 27 goes off due to expiration of the service life thereof or breakdown due to some other reason. The auxiliary light source 32 is constructed from a high intensity LED 32a in the illustrated embodiment (see FIG. 1). The extinguishment of the main light source 27 is detected by an optical sensor 39 and an extinguishment detection circuit 40, and an extinguishment detection signal is transmitted to the system controller 31 from the extinguishment detection circuit 40. The activation of the auxiliary light source 32 is controlled by an auxiliary light source drive circuit (auxiliary light source emission control device) 33 in the case where the auxiliary light source drive circuit 33 receives a signal (supplied from the system controller 31) to turn the auxiliary light source 32 ON. Note that the auxiliary light source drive circuit 33 operates at a constant-voltage current supplied from the stabilizing power source circuit 30.

The auxiliary light source drive circuit 33 moves the auxiliary light source 32 via an actuator 34 between a stand-by position, at which the auxiliary light source 32 is located outside of the main light path, and an operative position (auxiliary light emission position), at which the auxiliary light source 32 is opposed to (faces) the incident end face 25a in the main light path and emits light. The auxiliary light source 32 is normally held in the stand-by position outside of the main light path and normally does not operate.

Figure 2:
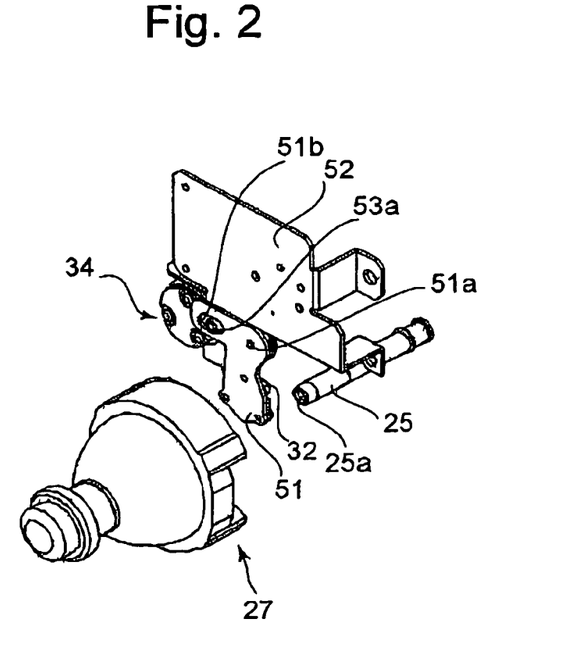
FIG. 2 is a perspective view of an auxiliary light source moving mechanism in a stand-by position of an auxiliary light source, according to the first embodiment of the present invention.
Figure 3:
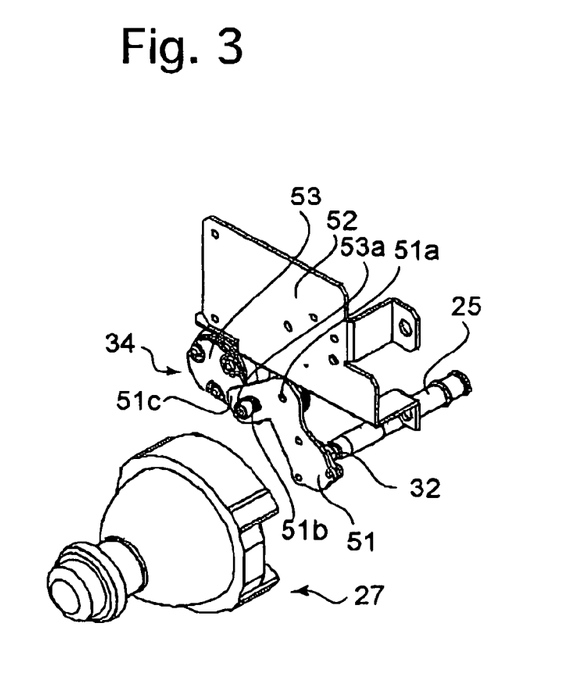
FIG. 3 is a perspective view of an auxiliary light source moving mechanism in an operative position of an auxiliary light source, according to the first embodiment of the present invention.

The mechanical structure of the light source apparatus will be discussed with reference to FIGS. 2 and 3. FIGS. 2 and 3 are perspective views of an auxiliary light source moving mechanism in the first embodiment of the present invention. In a stand-by position shown in FIG. 2, the main light source 27 emits light and in an auxiliary light emission position shown in FIG. 3, the auxiliary light source 32 is moved to the operative position and emits light.

The auxiliary light source 32 is secured to one end of an L-shaped lever 51. The L-shaped lever 51 is rotatably connected at a corner end thereof to a retainer plate 52 via a shaft 51a, and is connected at the other end thereof to the actuator 34. The actuator 34 is a rotary actuator which is provided with a rotary plate 53 which is connected to a rotating shaft (not shown) that is paralleled to the main light path and is provided with an eccentric shaft 53a. The eccentric shaft 53a is fitted in an elongated hole 51b formed in an arm 51c of the L-shaped lever 51 and extending along the arm 51c.

When no electricity is supplied to the actuator 34 in accordance with the control signal from the auxiliary light source drive circuit 33, the rotary plate 53 and the lever 51 are held in an initial position. This initial position corresponds to the normal position in which the auxiliary light source 32 secured to one end of the L-shaped lever 51 is held in the stand-by position out of the main light path.

When the actuator 34 is supplied with electricity in accordance with the control signal supplied from the auxiliary light source drive circuit 33, the rotary plate 53 is rotated in the clockwise direction (as viewed in FIGS. 2 and 3) by a predetermined angle and the eccentric shaft 53a which is fitted in the elongated hole 51b is moved, so that the L-shaped lever 51 rotates about the shaft 51a in a counterclockwise direction. As a result, the auxiliary light source 32 is moved to the operative position, i.e., the auxiliary light emission position in which the auxiliary light source faces the incident end face 25a. The auxiliary light source 32 is held in the operative position while the actuator 34 is supplied with electricity. When the auxiliary light source drive circuit 33 receives an auxiliary light emission signal from the system controller 31, the auxiliary light source drive circuit 33 supplies the auxiliary light source 32 with electricity to thereby turn the auxiliary light source ON and move the auxiliary light source 32 to the auxiliary light emission position.

Note that as the main light source 27 has a high temperature while emitting light, a cooling fan (not shown) is provided to cool the main light source 32. Furthermore, if the auxiliary light source 32 cannot be cooled sufficiently by circulation of the cooling air produced by the cooling fan, an auxiliary light source cooling device can be provided as necessary.

Since the auxiliary light source 32 is constructed from an LED in the illustrated embodiment, the amount of light emitted therefrom is smaller than that of the main light source. Therefore, even if the LED 32a is driven at a constant-current approximately equal to the absolute maximum rated value of forward current of the LED 32a to illuminate the body cavity, the brightness of the picked-up image is lower than when using the main light source 27, and hence, the image on the TV monitor is dark.

Figure 4:
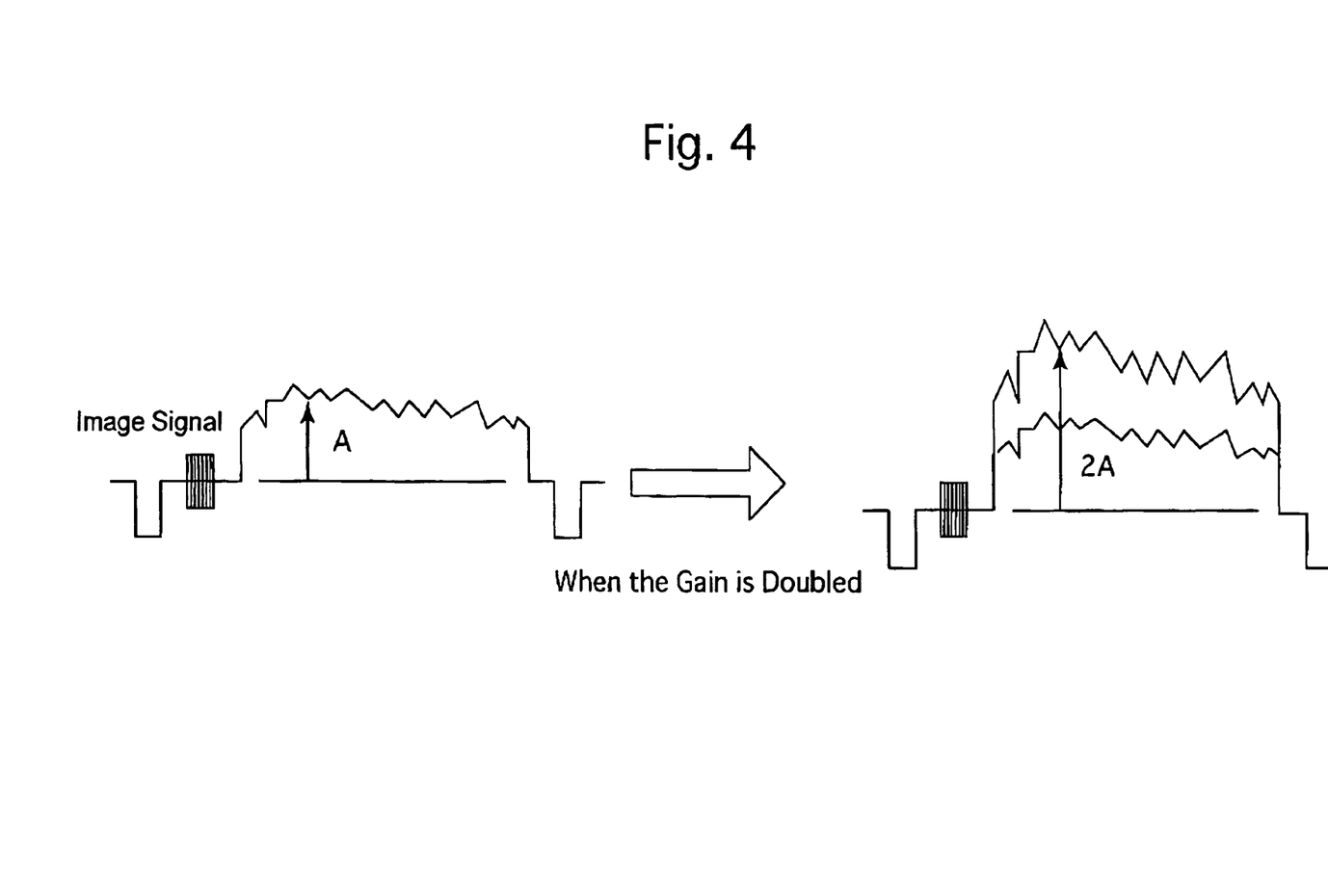
FIG. 4 is a timing chart of a gain increase when an auxiliary light source emits light in the first embodiment of the present invention.

In the first embodiment of the invention, when the light source apparatus is in an auxiliary light source emission mode, the selecting switch SW1 switches from the first amplifier OP1 to the second amplifier OP2 so that the gain can be doubled to obtain a bright image. FIG. 4 shows an image signal in the case where the second gain of the second amplifier OP2 is changed increased by double of that of the first gain of the first amplifier OP1.

Note that the gain in the auxiliary light source emission mode can be increased by double, triple, quadruple or more of that of the first gain of the first amplifier OP1. Also, the gain in the auxiliary light source emission mode can be less than double while the second gain of the second amplifier OP2 is larger than the first gain of the first amplifier OP1.

Figure 5A:
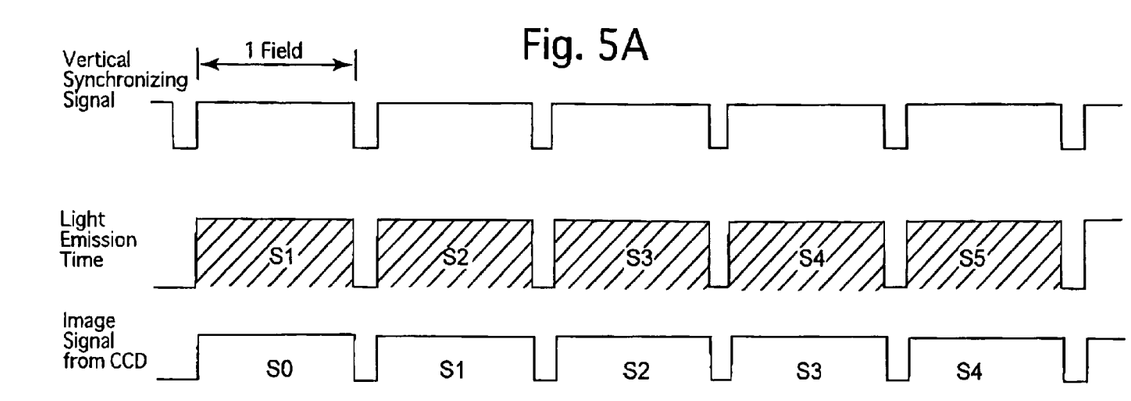
FIG. 5A is a timing chart showing a condition when a high-speed (normal) electronic shutter operation is operating, in a second embodiment of the present invention.
Figure 5B:
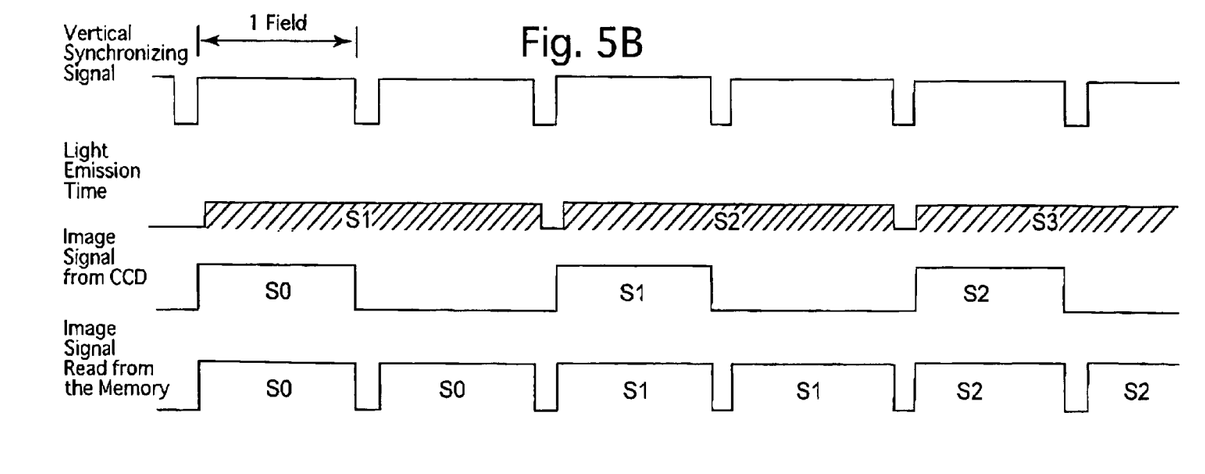
FIG. 5B is a timing chart showing a condition when an auxiliary light emits light and a low-speed electronic shutter operation is operating, in the second embodiment of the present invention.

In a second embodiment of the invention, when the light source apparatus is in an auxiliary light source emission mode, instead of switching from the first amplifier OP1 to the second amplifier OP2 to increase (double) the gain, an electronic shutter (not shown) is changed from a "high-speed shutter operation mode" to a "low-speed shutter operation mode" (prolonged exposure time). The timing chart of the high-speed and low-speed shutter operation modes are shown in FIGS. 5A and 5B, respectively. The image pickup device 16a of the electronic camera 16 repeats the exposure operation and the outputting operation of the picked-up image signals at a predetermined cycle of 1/60 seconds for one field (corresponding to NTSC system). At the high-speed shutter operation mode (normal electronic shutter operation mode) (FIG. 5A), the electronic shutter performs at a cycle shorter than 1/60 second (the shutter speed is higher than 1/60 sec). At the low-speed shutter operation mode, the electronic shutter performs at a longer cycle so that the exposure operation is carried out for two fields and the image signals are output every two fields. Consequently, it is possible to elongate the charge accumulating period of the picked-up image signals of each field in order to obtain a bright image.

FIG. 5A shows a timing chart when the shutter speed is at a slowest speed of 1/60 sec for the high-speed shutter operation mode. FIG. 5B shows a timing chart wherein the exposure time is prolonged; i.e., in the low-speed shutter operation mode wherein the shutter speed is 1/30 second for two fields. In the case shown in FIG. 5B, the image signals only for thirty fields are obtained per second, however, in this embodiment, the image signals for one field (corresponding to the time of the two fields stored in the memory 43) are read and output at a cycle of 1/60 seconds, and hence, a smooth motion picture can be displayed in the monitor TV without flickering or unnatural motion.

The electronic shutter speed at the low-speed shutter operation mode is not limited to the value mentioned above. For example, the exposure time can be prolonged so as to cover more than two fields, e.g., three fields, four fields or more, i.e., one field multiplied by an integer value. Moreover, the picked-up image signals can be output in synchronization with the synchronizing signal (vertical synchronizing signal) output at a predetermined cycle in order to simplify the control thereof. However, the image pickup time (exposure or charge accumulating time) can be a value other than one field multiplied by an integer value.

In a third embodiment of the present invention, the concepts of the first and second embodiments are combined. Namely, in the auxiliary light emission mode, the signal selecting switch SW1 switches from the first amplifier OP1 to the second amplifier OP2 to double the gain and change the electronic shutter mode to the low-speed shutter operation mode.

The operation in the third embodiment will be discussed below with reference to the flow chart shown in FIG. 6. The system controller 31 enters the emission control flow chart of FIG. 6 when the main power switch SWP is turned ON to supply electricity from a commercial power supply source 29.

Figure 6:
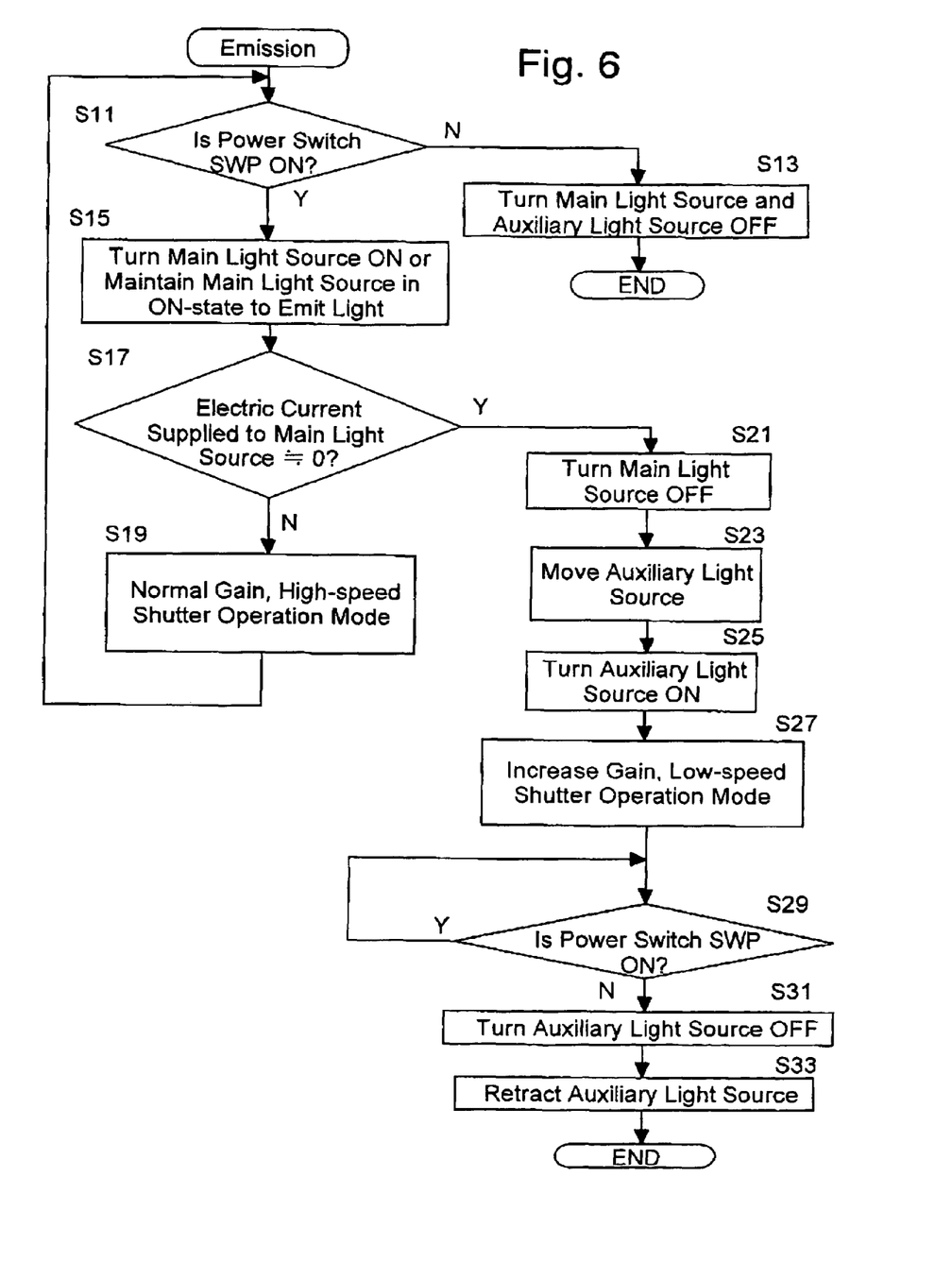
FIG. 6 is a flow chart of a light emitting operation of an electronic endoscope system in a third embodiment of the present invention.

In the sub-routine shown in FIG. 6, whether or not the power switch SWP is ON is checked (step S11). If the power switch SWP is not ON, the main light source 27 and the auxiliary light source 32 are turned OFF, and control ends (step S11, N; END).

If the power switch SWP is ON, the main light source 27 is turned ON, and the gain selecting switch SW1 is switched to the first amplifier OP1 to set the normal gain (high-speed shutter operation mode) so that the micro computer 45 performs the high-speed shutter operation, provided that the current of the main light source is not substantially zero (steps S11, Y; S15; S17, N; S19; S11). The operations mentioned above are repeated while the power switch SWP is ON and the main light source is supplied with electricity.

If the main light source 27 is out of order or the amount of the current of the main light source is reduced due to a safety device operating for some reason (step S17, Y), the main light source 27 is turned OFF (step S21), the actuator 34 is driven to move the auxiliary light source 32 to the operative position (step S23), and the auxiliary light source 32 is turned ON (S25). The gain is increased and the electronic shutter is switched to the low-speed shutter operation mode (step S27). The control does not proceed until the power switch SWP is turned OFF. If the power switch SWP is turned OFF, the auxiliary light source 32 is turned OFF and the actuator 34 is driven to retract the auxiliary light source 32 to the stand-by position and the emission operation ends (steps S29, Y; S31; S33; END).

When the auxiliary light source 32 is turned ON, a bright and clear image picked-up by the electronic camera 16 in the auxiliary light source emission mode can be viewed through the TV monitor. Accordingly, a user operates the operating portion 12 while viewing the TV monitor to remove the insertion portion 11 from the patient's body cavity, and turns the power switch SWP OFF. Thereafter, the main light source 27 can be replaced.

As can be understood from the above description, if the main light source 27 goes off for some reason, the auxiliary light source 32 is moved to the operative position and is turned ON to illuminate the body cavity in place of the main light source 27. At the same time, the gain of the image signals picked-up by the electronic camera 16 is enhanced or the electronic shutter speed of the electronic camera 16 is switched to the low-speed shutter operation mode, or both the enhancement of the gain and the change of the shutter speed are carried out to increase the amount of light emitted from the auxiliary light source 32 to thereby obtain a clear and bright image which can be viewed through the TV monitor. Furthermore, in the third embodiment, which is a combination of the first and second embodiments, makes it possible to prevent the gain of the image signal from being enhanced excessively, otherwise leading to production of outstanding noise signal in the image signal, or prevents the exposure time of the electronic shutter from being excessively increased, otherwise leading to an unacceptable color deviation or occurrence of outstanding flickering. Accordingly, a clear and bright image can be obtained.

As can be understood from the foregoing, the gain of the signal output from the image pickup device when the image signal is amplified is set higher in the auxiliary light source emission mode than that in the main light source emission mode, and accordingly, a clear and bright image can be obtained by the use of the auxiliary light source whose intensity is lower than the main light source.

According to an aspect of the present invention, since the low-speed shutter operation, in which the image pickup operation and output of the image signals are repeated at a cycle longer than the predetermined cycle when the main light source is activated, is carried out when the auxiliary light source is activated, the amount of light to be received is increased to thereby obtain a clear and bright image.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. An electronic endoscope system comprising:
   an electronic endoscope having an insertion portion;
   an image pickup device provided at a distal end of said insertion portion;
   an image signal processing device for converting a signal picked-up by and output from the image pickup device into an image signal;
   a main light source;

an auxiliary light source which emits less amount of light than the light emitted from the main light source, instead of the main light source; and a light guide member which guides illumination light emitted from one of the main light source and the auxiliary light source to the distal end of said insertion portion to thereby emit the illumination light from said distal end;

wherein, when the auxiliary light source emits the illumination light instead of the main light source, said image signal processing device sets the gain of said signal output from the image pickup device to a value higher than the gain of said signal when the main light source emits the illumination light, in order to process the image signal.

2. The electronic endoscope system according to claim 1, wherein said electronic endoscope system further comprises:

a processor unit to which the electronic endoscope is detachably attached, said processor unit being provided with said image signal processing device, said main light source and said auxiliary light source;

wherein said light guide member comprises a first light guide member provided in said electronic endoscope and a second light guide member provided in said processor unit, wherein said first and second light guide members are optically connected to each other when said electronic endoscope is attached to said processor unit.

3. An electronic endoscope system comprising:

an electronic endoscope having an insertion portion;

an image pickup device provided at a distal end of said insertion portion, an image signal processing device for converting a signal picked-up by and output from the image pickup device into an image signal which can be displayed by a display device;

a main light source;

an auxiliary light source which emits less amount of light than the light emitted from the main light source, instead of the main light source; and a light guide member which guides illumination light emitted from one of the main light source and the auxiliary light source to the distal end of said insertion portion to thereby emit said illumination light from said distal end;

wherein said image signal processing device performs a high-speed shutter operation in which the image pickup operation and the image signal output operation are repeated at a predetermined cycle when the main light source emits said illumination light; and performs a low-speed shutter operation in which the image pickup operation and the image signal output operation are repeated at a cycle longer than said predetermined cycle when said auxiliary light source emits said illumination light instead of said main light source.

4. The electronic endoscope system according to claim 3, wherein when said image signal processing device performs said low-speed shutter operation, the image pickup operation and the image signal output operation are repeated at a cycle which is represented said predetermined cycle multiplied by an integer value.

5. The electronic endoscope system according to claim 4, wherein said image signal processing device comprises a memory for storing the picked-up image signals for at least one field, so that when said image signal processing device performs said low-speed shutter operation, the stored image signals for said at least one field are read at said predetermined cycle and are converted into image signals which can be displayed by said display device.

6. An electronic endoscope system comprising:

an electronic endoscope having an insertion portion;

an image pickup device provided at a distal end of said insertion portion, an image signal processing device for converting a signal picked-up by and output from the image pickup device into an image signal;

a main light source;

an auxiliary light source which emits less amount of light than the light emitted from the main light source, instead of the main light source; and a light guide member which guides illumination light emitted from one of the main light source and the auxiliary light source to the distal end of said insertion portion to thereby emit said illumination light from said distal end;

wherein, when the main light source emits the illumination light, said image pickup device operates at a high-speed shutter operation mode in which the image pickup operation and the image signal output operation are repeated at a predetermined cycle, so that said image signal processing device processes the image signal output from the image pickup device after the image signal is amplified at a first gain; and when the auxiliary light source emits the illumination light instead of the main light source, said image pickup device operates at a low-speed shutter operation mode in which the image pickup operation and the image signal output operation are repeated at a cycle longer than said predetermined cycle, so that said image processing device processes the image signal output from the image pickup device after the image signal is amplified at a second gain higher than the first gain.

* * * * *